June 25, 1940. H. E. TRAVER Plant Pat. 406
BEGONIA
Filed Jan. 26, 1939
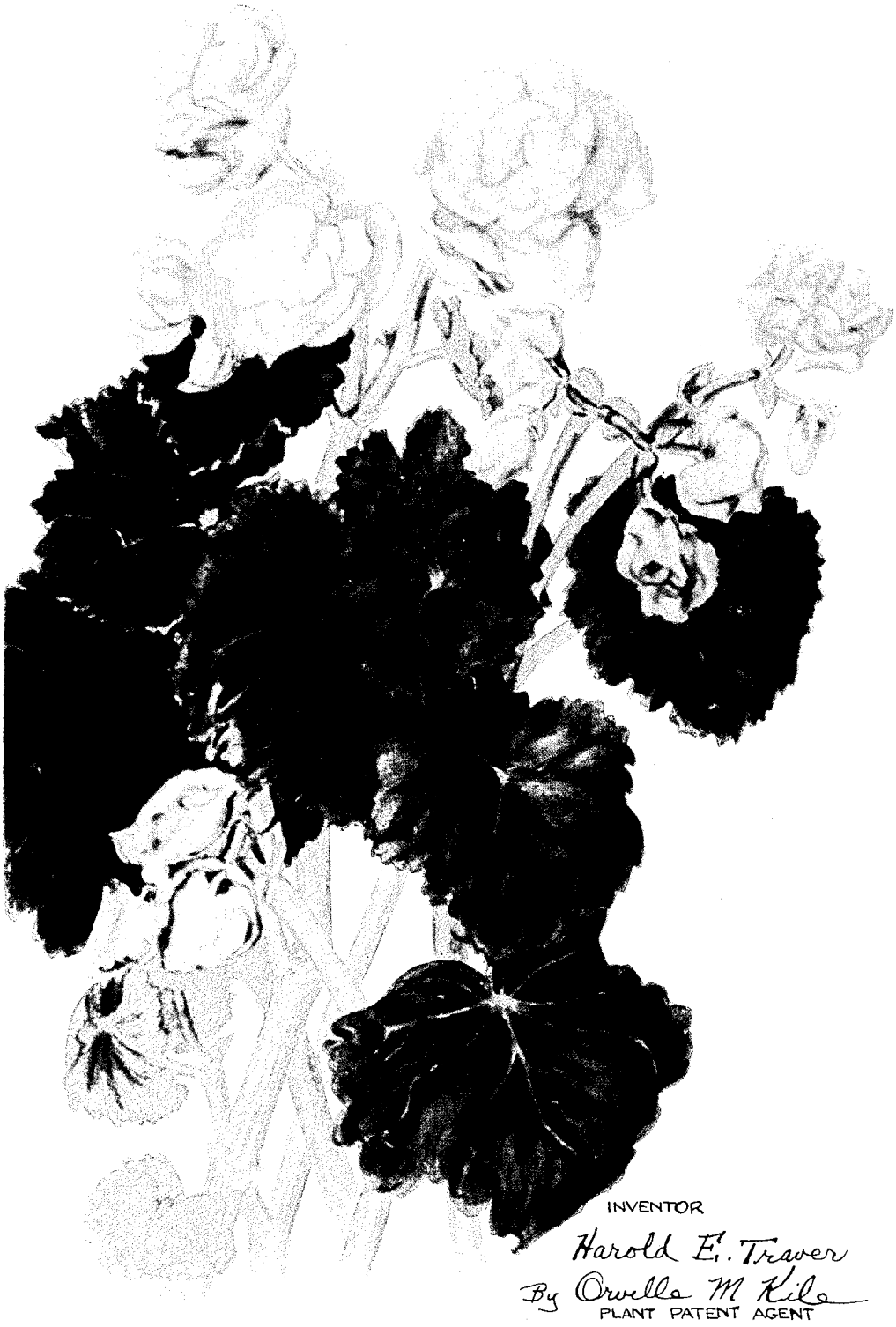
INVENTOR
Harold E. Traver
By Orville M Kile
PLANT PATENT AGENT Patented June 25, 1940

Plant Pat. 406

UNITED STATES PATENT OFFICE

406

BEGONIA

Harold E. Traver, Woodbury, Conn.

Application January 26, 1939, Serial No. 252,960

1 Claim. (Cl. 47—60)

My new variety of begonia is of the winter flowering hybrid type and is a sport of Melior. It was discovered by me in my greenhouses in Connecticut several years ago. I had some Melior begonias in flower at Christmas time and carried the plants over until spring. When these same plants began to make their new growth in the spring, I noticed that the leaves on one of the branches were somewhat different from the old type Melior so I propagated cuttings from this branch. Asexual reproduction since that time has shown the characteristics to be firmly fixed.

The varieties known to me which are most like this new variety are its parent and Lady Mac, the latter also a sport of Melior. It differs from these two varieties in many respects, particularly in that the new variety has double flowers of 18 to 28 petals while the other varieties have only single flowers of 4 petals. The scarlet color of the double blossoms, the dark green of the foliage, and the compactness of growth combine to make an especially handsome Christmas plant. The flowers retain their brilliant color until they drop off, and the foliage is perpetually a dark glossy green.

This new variety is a very vigorous grower and does exceptionally well after being pinched back. Its many blossoms are evenly spread over the entire plant throughout the blooming season.

The original illustrations accompanying this application show a section taken from a full-grown plant of the new variety, and they depict the buds, blossoms, stems and leaves in approximately their true size and colors. There is a glossiness of the natural leaves and flowers which cannot be shown by water colors, however. A mature plant is composed of many of these main branches issuing from the crown growth which forms at the end of the rooted leaf-stem cutting.

Following is a detailed description of this new variety of begonia. Color plate references are to Ridgway's Color Standards and Nomenclature. Where any colors are given without plate references, the ordinary dictionary term is intended.

*The plant*

Growth: Growth is very clean, sturdy and heavy. The mature plant is very compact and attains a height of from 16 to 18 inches. A crown is formed at the end of the rooted cutting and the roots form from this crown. The plant can successfully be "pinched back" or "stopped" so as to produce lateral shoots of foliage and bloom.

Blooming: Blooms abundantly from October 15 to January 15 or later, depending upon when the cuttings are taken.

Foliage: Abundant; overlapping.

*Leaves.*—*Shape*—palmately veined; almost round except for a deep lobe at the base. *Edges*—undulate with broad serrations approximately crenate. *Appearance*—smooth and glossy. Ribs less pronounced than usual in begonias of this type. *Size*—varying in size, largest about 5 to 6 inches across. Averages about the same sizes as Melior, its parent. *Color*—upper surface Dark Cress Green (Plate XXXI), with Cress Green (Plate XXXI) veining and indefinite splotches or shadings. Veins on under surface are Light Cress Green (Plate XXXI). Intervenous section on under surface is Light Cress Green tinged and considerably overlaid with Deep Corinthian Red (Plate XXVII) to Pompeian Red (Plate XIII). Frequently the edges are likewise tinged with the same Deep Corinthian Red to Pompeian Red. *Texture*—heavy.

*Stems.*—*Main stalks*—several main shoots arise directly from the root crown and lateral shoots break from these. Exceptionally heavy. *Color*—Rainette Green (Plate XXXI), with reddish brown tinge, approximately Ochre Red (Plate XXVII) to Etruscan Red (Plate XXVII) on mature plants.

*Leaf stems.*—Chrysolite green (Plate XXXI), with a tendency on mature leaves to have a reddish overlay which is approximately Ochre Red to Etruscan Red (Plate XXVII).

*The flower*

Bud:

*Color.*—Scarlet Red (Plate I).

*Shape.*—Flattened; somewhat heartshaped.

Flower: All male, so far as known; double; sterile.

*Size.*—1½ to 2 inches in diameter.

*Petalage.*—18 to 28 petals. At the beginning of the blooming season the flowers are semi-double, but when the plant is fully developed the flowers are very double. This is a natural trait and requires no special cultivation to produce it. *Petals*—*color*—Scarlet (Plate I). As the opened flower ages, the central petals lighten slightly and they are then Peach Red (Plate I) edged with Scarlet (Plate I). The under side of the petals is slightly lighter than the upper side. *Appearance*—velvety on inner surface of outer petals; remaining portions silky and more glossy.

*Arrangement.*—The flowers form in sprays, having from 5 to 10 flowers in a spray. The sprays are distributed over the entire plant.

*Pedicels.*—Chrysolite Green (Plate XXXI), with a slight reddish overlay approximately Ochre Red to Etruscan Red (Plate XXVII).

*Bracts.*—Two small reddish bracts are found at the base of each pedicel. When the blossom falls, the bracts remain and have the appearance of tiny leaves.

*Stamens.*—Entirely lacking.

*Comparison with Melior and Lady Mac*

The begonia varieties known to me, which are most like my new variety are Melior and Lady Mac. There are a number of differences, the principal ones being given below.

1. The blossoms of my new variety are double while those of Melior are single.

2. The blossoms of my new variety are sterile, which is not true of Melior.

3. The blossoms of my new variety are scarlet and those of Melior are pink.

4. The blossoms of my new variety are larger than those of Melior.

5. The leaves of my variety are of heavier texture.

6. Edges of the leaves of my new variety are undulate with broad serrations while those of Melior are merely serrate.

7. The leaves of my variety are darker in color and the veining is less pronounced.

8. Growth of my variety is cleaner, sturdier and heavier.

9. The main shoots of my variety are heavier.

10. Both main and lateral shoots of my new variety show on the mature plants a reddish tinge from Etruscan Red (Plate XXVII) to Pompeian Red (Plate XIII), whereas those of Melior show no reddish tinge.

Since Lady Mac is like Melior in all but color, the above comparison will also apply as a comparison between my new variety and Lady Mac.

Having thus disclosed my discovery, I claim:

A new and distinct variety of winter-blooming begonia plant of the Melior type, characterized particularly by its glossy, dark green, heavy-textured leaves which are undulate rather than merely serrate and which have veins of little prominence; its exceptionally heavy main stems; its compact, sturdy and heavy crown growth; and its very large, double, sterile blossoms of scarlet produced in abundance continuously for at least four months, under ordinary greenhouse conditions.

HAROLD E. TRAVER.